(12) United States Patent
Constantinescu et al.

(10) Patent No.: US 8,349,924 B2
(45) Date of Patent: Jan. 8, 2013

(54) FIRE-RESISTANT PLASTICIZER FOR THE PLASTIC MATERIAL INDUSTRY AND METHOD OF MAKING THEREOF

(75) Inventors: Anton Constantinescu, Painesville, OH (US); Jose Reyes, Newtown, PA (US)

(73) Assignee: JJI Technologies, LLC, Painesville, OH (US)

( * ) Notice: Subject to any disclaimer, the term of this patent is extended or adjusted under 35 U.S.C. 154(b) by 0 days.

(21) Appl. No.: 12/688,791

(22) Filed: Jan. 15, 2010

(65) Prior Publication Data
US 2010/0184890 A1  Jul. 22, 2010

Related U.S. Application Data

(60) Provisional application No. 61/145,500, filed on Jan. 16, 2009, provisional application No. 61/154,351, filed on Feb. 20, 2009, provisional application No. 61/288,305, filed on Dec. 20, 2009.

(51) Int. Cl.
C07C 43/205 (2006.01)
C08G 59/62 (2006.01)
C08K 3/20 (2006.01)
C08K 5/17 (2006.01)
C08K 5/3492 (2006.01)

(52) U.S. Cl. ........ 524/100; 524/252; 524/436; 524/437; 528/110; 528/111; 568/648

(58) Field of Classification Search ................. 524/100, 524/436, 437, 252; 528/110, 111; 568/648
See application file for complete search history.

(56) References Cited

U.S. PATENT DOCUMENTS

| 2,434,797 A | 1/1948 | Harvey |
| 2,519,013 A | 8/1950 | Banigan |
| 3,007,888 A | 11/1961 | Mack et al. |
| 3,074,900 A | 1/1963 | Wasserman |
| 3,189,510 A | 6/1965 | Eldred |
| 3,274,301 A | 9/1966 | Kulp |
| 3,486,966 A | 12/1969 | Allen et al. |
| 4,195,001 A | 3/1980 | Lytton |
| 4,886,893 A | 12/1989 | Meffert et al. |
| 5,367,006 A | 11/1994 | Hermansen et al. |
| 6,548,189 B1 | 4/2003 | Gunasekaran et al. |
| 7,084,103 B1 | 8/2006 | Springsted et al. |

FOREIGN PATENT DOCUMENTS

| GB | 628358 A1 | 8/1949 |
| GB | 1279258 B1 | 6/1972 |
| WO | 0034219 A1 | 6/2000 |

OTHER PUBLICATIONS

Kamath, et al., "Plasticizers Based on Epdxidized Cashew-Nut-Shell Liquid", Current Science 1963, vol. 32, No. 72-3, Publisher: University of Bombay.
Agrawal et al., "Cardanol-Based Epoxy Flexibilizers for Inhibition of Composite Propellants", 1993, pp. 19-34, vol. A30, No. 1, Publisher: Journal of Macromolecular Science, Pure and Applied Chemistry.
Jagannath, J.H., "Optimization of Type and Amount of Dilutents and Flexibilizers for Solventless Epoxy Coatings", Proceedings of the Waterborne, High Solids, and Powder Coatings Symposium 1995, pp. 298-309, No. 22nd, Publisher: University of Southern Mississippi, Dep of Polymer Science.

*Primary Examiner* — Kriellion Sanders
(74) *Attorney, Agent, or Firm* — Edwin A. Sisson, Attorney at Law, LLC

(57) ABSTRACT

The present invention relates to a group of new plasticizers for thermoplastics such as polypropylene, copolymers of polypropylene, polyethylene, polyethylene terephthalates, polystyrene and/or other polymers or mixtures of polymers containing organic and/or inorganic fillers, where the plasticizer is used for obtaining polyvinyl chloride like aspects and improved processability as well as for obtaining a better flexibility and a lower energy consumption during the processing step.

20 Claims, 2 Drawing Sheets

FIRE-RESISTANT PLASTICIZER FOR THE PLASTIC MATERIAL INDUSTRY AND METHOD OF MAKING THEREOF

PRIORITIES AND CROSS REFERENCES

This application claims priority from U.S. Provisional Patent Application Nos. 61/145,500, filed 16 Jan. 2009, 61/154,351; filed 20 Feb. 2009, and 61/288,305, filed 20 Dec. 2009.

FIELD OF THE INVENTION

This invention relates to plasticizers for thermoplastics and mixtures thereof.

BACKGROUND

Presently the plastics industry is facing a new challenge: the replacement of polyvinyl chloride (PVC) from almost all the compositions that are being currently used in the industry with alternate plastic compositions that do not present direct toxicity during their combustion.

One of the most important aspects of PVC replacement consists of obtaining compositions that can imitate the quality of PVC's softness and processability while eliminating or reducing its disadvantages of the high toxicity of the by-products that result from the combustion of PVC.

Present solutions have given unsatisfactory results in their applications.

SUMMARY

This specification describes a novel class of plasticizers to be used as an additive for plasticizing polymer mixtures, for diminishing the amount of energy used in the processing of polymer mixtures containing inorganic and/or organic fillers, for improving the tensile strength of the resulted mixtures, for increasing the extrudability of complex mixtures and for other physicochemical effects.

The plasticizers disclosed are the reaction products of an alcohol, or alcohols, or an amine or amines or mixture thereof with an epoxidized molecule having at least 15 carbon atoms and 1 to 3 double bonds. It is further disclosed that the expoxidized molecule be an epoxidized cardanol of the formula

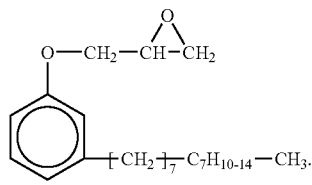

and the number of hydrogens in the 15 carbon aliphatic chain in the meta position depends upon the number of conjugated double bonds, the number which is selected from the group consisting of 1, 2, and 3 and in the case of an alcohol, the alcohol is preferably selected from the group consisting of ethanol, isopropyl alcohol, and tert-butyl alcohol, and in the case of amines, preferably diethanol amine.

Also disclosed is that the plasticizer may be present in a composition of the plasticizer and a thermoplastic compound. It is further disclosed that the thermoplastic compound is polypropylene, a copolymer of polypropylene, high density polyethylene, a polyethylene terephthalate or polyethylene terephthalate copolymer. It is further disclosed that the plasticizer is present from about 1 to about 12 weight percent of the total composition.

It is also disclosed that the composition may further comprise a flame retardant composition or compound selected from the group consisting of a melamine, a diamine, magnesium hydroxide, aluminum hyrdoxide and that the flame retardant composition or compound may be present at up to 80 parts of the flame retardant composition to 20 parts of the thermoplastic polymer.

Also, disclosed is a process for the manufacture of a plasticizer compound comprising the steps of heating a mixture of an epoxidized oil and alcohol, in the presence of an acid catalyst and reacting the epoxidized oil with the alcohol until less than 10% of epoxidized oil remains, and removing the excess alcohol. However, the final solution is preferably essentially void of unreacted epoxidized cardanol, meaning the epoxide number is about 0 or is 0. It is also disclosed that the heating can be done at reflux conditions.

DETAILED DESCRIPTION

Disclosed in this specification is a new class of plasticizers that can be used in thermosetting, thermoplastics, thermoplastic polymer matrices, copolymers, terpolymers, coatings, paints, films, resins binders, fibers and articles formed from the same.

The thermoplastics include but are not limited to such polymers as polypropylene, copolymers of polypropylene, polyethylene, copolymers of polyethylene, high and low density polyethylene, polyethylene terephthalates and its copolmers, also known as PET, polystyrene and/or other polymers or mixtures of polymers containing organic and/or inorganic fillers.

Also disclosed in this specification are novel compounds and methods of forming different types of compounds when reacting various epoxides of cardanol with alcohols, amines, acids or other functional compounds that impart a high temperature resistance for the resulting chemical compounds.

Cardanol is the extracted oil from the cashew nutshell. Cardanol is used to describe the decarboxylated derivatives made from the thermal decomposition of any of the naturally anacardic acids. This includes more than one compound because the composition of the side chain R varies in its degree of unsaturation. Tri unsaturated cardanol is the major component and is usually present at about 41%. The remaining cardanol is about 34% mono-unsaturated with 22% bi-unsaturated, and 2% saturated.

One of cardonal's formula is $C_6H_4(OH)-(CH_2)_7-CH=CH-CH_2-CH=CH-(CH_2)_2-CH_3$ Epoxidized cardanol can be made in many ways. One way is with epichlorohydrin, in the presence of a base.

Epoxidized cardanol made with epichlorohydrin has the following formula:

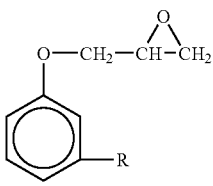

having R in the meta position where R is a 15 carbon atom aliphatic chain having one, two or three non-conjugated double bonds and has the formula $[CH_2]_7$—$C_7H_{10\text{-}14}$—$CH_3$. The number of hydrogens in R will vary depending upon the number of non-conjugated double bonds.

Figure 1:
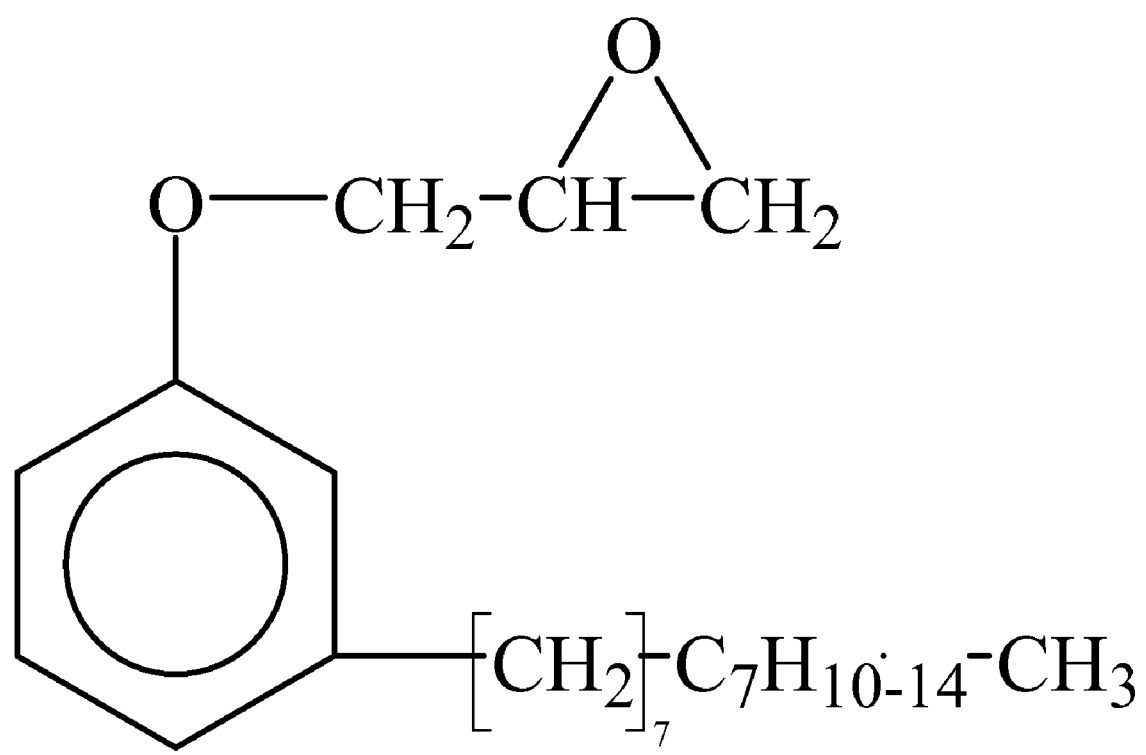
FIG. 1 is a structural formula of epoxidized cardanol.

Cardanol has several naturally occurring isomers. Therefore, the epoxidized cardanol has been characterized in the following formula and shown in FIG. 1 as

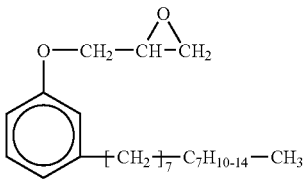

See for example, "Phenalkamine Multipurpose Epoxy Resin Curing Agents", by Dai et al, Cardolite Corporation, SPI-ERF Conference, 1994.

A commercial example of an epoxidized cardanol is Cardolite® NC-513 from Cardolite Corporation, Newark, N.J. 07105 and has the following formula:

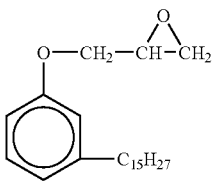

Compounds made in both ways can be used in the reaction to give plasticizers of the aforementioned nature.

When reacted with an alcohol, the following compounds are obtained.

In the general sense, the compound is

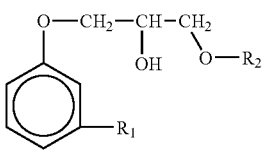

where $R_1$ is a 15 carbon atom aliphatic chain containing one, two or three non-conjugated double bonds and has the formula $[CH_2]_7$—$C_7H_{10\text{-}14}$—$CH_3$ and $R_2$ is selected from the group consisting of alkyls and aryls, or mixtures thereof with or without one or more functional groups. The bond of the oxygen to the carbon may be any carbon of the $R_2$ species.

Figure 2:
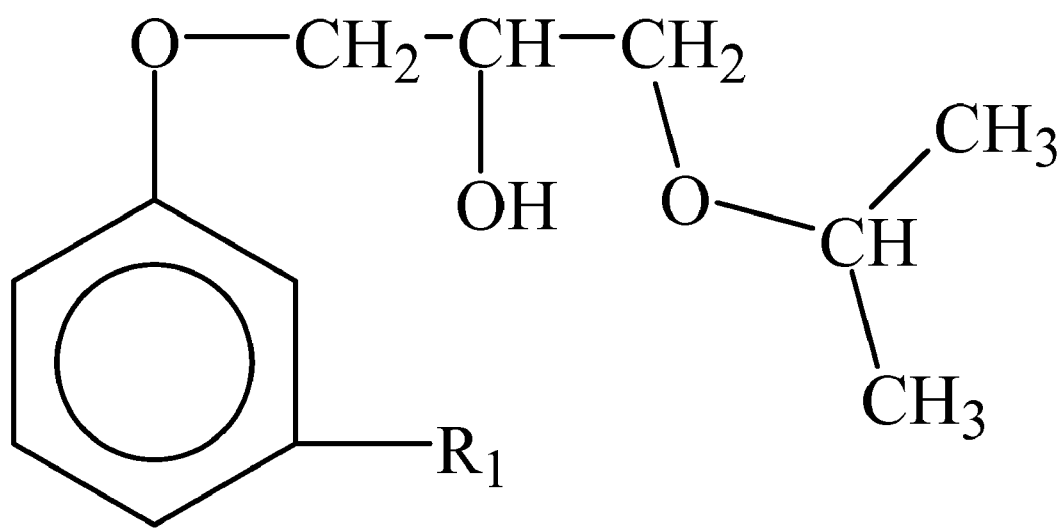
FIG. 2 is a structural formula of the reaction product of epoxidized cardanol with isopropyl alcohol.

When reacted with isopropyl alcohol, the structure, as shown in FIG. 2, is

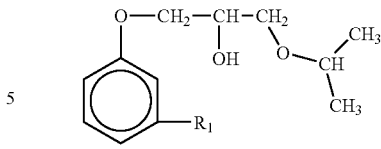

This compound's chemical name is 2-propanol, 1-(1-methylethoxy)-, 3-(cashew nutshell liq. oxy) derivs.

The alcohol reacted with the epoxidized cardanol can be selected from the group consisting of aliphatic or substituted alcohols with one or more functional groups in addition to the hydroxyl group, alkyl alcohols with one or more functional groups in addition to the hydroxyl group, and aryls with one or more functional groups in addition to the hydroxyl group. The alcohol can also be selected from the group consisting of methanol, ethanol, propanol isomers, and butanol isomers.

It is also known that the reaction of the epoxidized cardanol with an alcohol in the presence of an acid, in this case phosphoric acid, will create two additional species believed present in the composition. These are

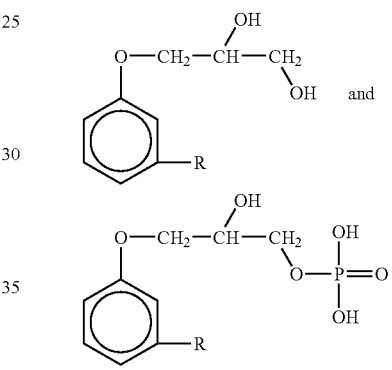

Where R in both instances is a 15 carbon atom aliphatic chain containing one, two or three non-conjugated double bonds and has the formula $[CH_2]_7$—$C_7H_{10\text{-}14}$—$CH_3$.

The plasticizer aspect of the new molecule is based upon the discovery that when used in a polymer/filler mixture, it lowers the viscosity of the composition and increases greatly the amount of fire-retardant or any other organic/inorganic filler that can be added to the mixture, it increases the its extrudability, it increases the elongation at the breaking point, it changes the aspect of the extrudate which becomes similar to that of polyvinyl chloride (PVC).

EXPERIMENTAL

Example I

Plasticizer 1 was made introducing 1000 grams of epoxidized cardanol (Cardolite® NC-513) into a round bottom flask provided with a stirring, heating and cooling system. Approximately 1 L of ethanol was added to the flask at room temperature, approximately 25° C. The stirring process was started, approximately 25 grams of phosphoric acid was gradually added to the flask, and the mixture heated at atmospheric reflux conditions for 3 hours. (It should be noted that methanesulphonic acid or other acidic catalysts are believed suitable as well.)

The excess of ethanol was eliminated by simple distillation. The traces of ethanol remaining in the mixture were then eliminated by applying high vacuum at a temperature of 120° C. for at least 3 hrs. At least 90% of the epoxidized cardanol should be reacted, or alternatively 10% of the epoxidized cardanol or less may remain in the solution. Preferably however, the reaction product should be preferably essentially void of unreacted epoxidized cardanol, or essentially free of unreacted epoxidized cardanol, which means that there could be some trace amounts of unreacted epoxidized cardanol. One measure is the epoxide number and an epoxide number of about 0, or 0 is considered essentially void of, essentially free of unreacted epoxidized cardanol.

The liquid, as it results with or without any neutralizing agent, was mixed in the complex plastic mixtures which may or may not contain fire retardants, organic fillers and/or inorganic fillers. The epoxidic ring can be attacked by the nucleophile in either location, nevertheless for simplicity, we have shown only the major compounds formed.

A variant of this reaction implies a reverse order addition. 25 grams of acid catalyst, either methanesulphonic acid, phosphoric acid or other acids, is added to one liter of ethanol. Then, after increasing the temperature of this solution to about 40° C., one kilogram of the epoxidized cardanol is gradually added.

The resulting compound can be described as the reaction product of epoxidized cardanol and ethanol. As shown in TABLE II, it is believed that other alcohols work as well, therefore this class of pasticizers can be called the reaction product of epoxidized cardanol with at least one alcohol.

This material can be compounded with a polyolefinic compound with or without the presence of a thermoplastic polyolefin (such as Engage® (The DOW Chemical Company, USA or Kraton® (KRATON Polymers U.S. LLC) polymers), in the preferred range of 0.5-12 percent by weight of the composition.

The plasticizing property is demonstrated in Table I—Properties of Plasticizer 1 in Polypropylene. The properties indicated were measured on a mixture of polypropylene (Marlex® ALN-070 Chevron Phillips Chemical Company, LLC USA, which is an impact copolymer of high strength and already lubricated) with Plasticizer 1, at the levels indicated.

TABLE 1

Properties of Plasticizer 1 in Polypropylene

| | Control | Exp 1 | Exp 2 | Exp 3 |
|---|---|---|---|---|
| Plasticizer (wt %) | 0 | 5 | 7 | 9 |
| Polypropylene (wt %) | 100 | 95 | 93 | 91 |
| Melt Flow (g/10 min @ 230° C.) | 6.64 | 7.96 | 10.42 | 10.84 |
| Hardness (Shore A) | 96.3 | 94.6 | 95.2 | 94.8 |
| Tensil (psi) | 2881 | 1791 | 2400 | 2421 |
| Elongation (%) | 17.6 | 179.12 | 406.93 | 403.95 |

Plasticizer 1 also enabled loading of optional flame retardants at levels previously not achievable. For example, Plasticizer 1 was used at 7 wt % of the composition and the loading of 65% Magnesium hydroxide was achieved in high density polyethylene. This is approximately 20% higher than the loading without the plasticizer. The composition can also be halogen free.

An optional flame retardant powder mixture can be added and is described as a nitrogenous phosphate or sulfonate formed in the presence of a char catalyst. The nitrogenous phosphate or sulfonate component may be formed using any of the conventional techniques with the char catalyst being introduced at least in part prior to the formation of the final product. For example, the char catalyst may be introduced either in total or in part with one or more of the nitrogen containing compounds and then have the phosphorus or sulfur containing compound reacted in. These nitrogenous phosphate or sulfonate components may also be formed by introducing parts of one or more of the reactants in steps. For example, a portion of the total amount of the nitrogen containing reactant may be added to a portion of the activator followed by a portion of the phosphorus or sulfur containing reactant and then repeated in any order and in as many steps as desired to obtain the final activated flame retardant.

The selection of the nitrogen containing reactant and the phosphorus or sulfur containing reactant used can depend upon the application. Suitable reactants include those known for use in forming nitrogenous phosphate or sulfonate flame retardants, for example, ammonium phosphate, ammonium pyrophosphate, ammonium polyphosphate, ethylene-diamine phosphate, piperazine phosphate, piperazine-pyrophosphate, melamine phosphate, dimelamine phosphate, melamine pyrophosphate, guanidine phosphate, dicyanodiamide phosphate urea phosphate, ammonium sulfonate, ammonium polysulfonate, ethylenediamine sulfonate, dimelamine suflonate, guanidine sulfonate, and dicyanodiamide sulfonate. For example, suitable nitrogen containing reactants include ammonium, alkyleneamines (including diamines), triazine, melamine, melam, melem, melon, ammeline, ammelide, 2-ureidomelamine, acetoguanamine, benzoguanamine, guanidine, dicyanodiamide, diamine phenyltriazine or mixtures thereof. Preferred nitrogen containing reactants include melamine, ammonium, and ethylene diamine. Examples of suitable phosphorus or sulfur containing reactants include phosphoric acid and sulfonic acid.

The char catalyst is a component that often enhances the performance of the nitrogenous phosphate and/or sulfonate component and preferably is a char forming catalyst or a phase transfer agent or a combination of both. The char catalyst can be present in the flame retardant in any amount that provides the acceptable enhanced flame retardancy, for example up to 5, 8 or 10 wt % and as little as 0.01, 0.1 and 0.2 wt %. It is preferred to use both a char forming catalyst and a phase transfer catalyst together these may be present in the flame retardant in an amount between 0.1, preferably 0.3, and 3.0, preferably 2.5 wt %, based on the total weight of the flame retardant.

Although not wishing to be bound by any particular theory, it is believed that the char forming catalyst may act, at the time of decomposition of part of the system, to "grab onto" or react with decomposing molecules, thereby minimizing the production of low molecular weight components that can burn. This it is believed generally enables the development of char rather than burn. Consequently, exemplary char forming catalysts include multi-cyclic compounds having at least one reactive group in each of at least two rings. Typically, the rings are joined together by atoms common to both rings. These may include spiro-compounds. For example, the spiro compounds can define at least two heterocyclic ring structures, e.g., that each include oxygen, joined by at least one carbon atom common to both rings.

Preferred char forming catalyst include spiro-compounds represented by the following formula I:

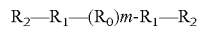

where m represents a number between 1 and 8, for example less than 3 or less than 2; $R_0$—independently represent a di-tri-, or quad-valent radical including two independently substituted or unsubstituted, saturated or unsaturated heterocyclic ring structures joined by at least one common carbon atom and preferably no more than two, for example one, carbon atoms common to the heterocyclic ring structures; $R_1$ —independently represents a bond; or a substituted or unsubstituted, saturated or unsaturated hydrocarbyl or heterocarbyl linking group, preferably a $C_1$-$C_6$ alkyl linking group, for example a $C_3$ alkyl; and $R_2$ —independently represents a terminal group, preferably a terminal amine for example a primary amine.

Exemplary compounds include those in which the heterocyclic ring structure comprises at least two heteroatoms in at least two heterocyclic ring structures, and/or $R_0$ independently represents a divalent radical, preferably with at least one, for example, two (including two adjacent), heterocyclic ring structures being 6-member. These compounds may also include those in which the heteroatom in the heterocyclic rings is predominately oxygen.

The preferred char catalyst includes those having a molecular weight of at least 180, preferably at least 200 and/or a flash point of greater than 200° C.

Some preferred embodiments include one or more tetraoxaspiro materials, such as derivatives of a tetraoxaspiro undecane (e.g., amine derivatives), such as one or more 2,4,8,10-tetraoxa-spiro[5.5]undecane compounds and/or one or more 1,5,7,11-tetraoxa-spiro[5.5]undecane compounds.

The char forming catalyst component may also include adducts, for example, amine adducts, nitrile adducts (including 2-propenenitrile or acrylonitrile) and/or oxirane adducts (including butoxymethyl oxirane). 2,4,8,10-tetraoxaspiro[5.5]undecane-3,9-dipropanamine with an amine or nitrile adduct, such as acrylonitrile is a specific example.

The phase transfer agent utilized can be or can include tetrahydrocarbyl ammonium salts, for example, tetramethyl, tetraethyl, tetrapropyl, tetralkyl, and/or aryltrialkyl ammonium salt in which the salt is a bromide, chloride, hydroxide and/or hydrogen sulfate ammonium salt. Preferably, the phase transfer catalyst includes phosphate esters, tetraethylammonium bromide, tetraethylammonium hydroxide, tetrapropylammonium bromide, tetrabutyl ammonium bromide, tetrabutyl ammonium hydroxide, tetrabutyl ammonium hydrogen sulfate and/or benzyltriethyl ammonium chloride.

An exemplary retardant may be prepared as follows.

To 900 grams of water, while under agitation, add 180 grams of ethylene diamine, 60 grams of melamine and 0.5 wt percent by finished recovered product of 2,4,8,10-tetraoxaspiro[5.5]undecane-3,9-dipropanamine adduct with 2-propenenitrile (acrylonitrile), which is commercially available from Ajinomoto, Inc. under the tradename YSE-CURE B-001. The mixture is warmed to 77° C. and, while maintaining temperature, phosphoric acid is slowly added until a pH of 7.0 is reached. The mixture is cooled, filtered, dried and ground to recover the flame retardant.

One of ordinary skill can easily modify the above technique to achieve a preferred ratio of 80:20 ethylene diamine phosphate to melamine phosphate.

This flame retardant can be present in amounts ranging from about 15 to about 85% by weight of the total composition. The char forming catalyst will therefore be present in the insulative wall in amounts ranging from about 0.15 weight percent to about 8.5 weight percent.

The compound described above can be described as the reaction product of epoxidized cardanol and ethanol. Other alcohols will work as well, as described in the following table:

TABLE II

Examples of Epoxidized Cardanol Reactions with Alcohols

| Plasticizer ID | Starting Material | Catalyst | Reactant |
|---|---|---|---|
| Ex - 2 | NC-513 ® (370 g) | Phosphoric Acid (20.7 g) | t-BuOH (200 g) |
| Ex - 2 | NC-513 ® (800 g) | Phosphoric Acid (0.8 g) | EtOH (800 mL) |
| Ex - 3 | NC-513 (400 g) | Methanesulfonic Acid (10 mL) | EtOH (800 mL) |
| Ex - 4 | NC-513 ® (200 g) | Phosphoric Acid (6.25 g) | EtOH (200 g) |
| Ex - 5 | NC-513 ® (300 g) | p-toluenesulfonic acid (3 g) | EtOH (300 g) |
| Ex - 6 | NC-513 ® (300 g) | None | Diethanol amine (200 g) |
| Ex - 7 | NC-513 ® (600 g) | Phosphoric acid (19 g) | IPA (400 g) |
| Ex - 8 | NC-513 ® (600 g) | p-toluenesulfonic acid (9 g) | IPA (400 g) |
| Ex - 9 | NC-513 ® (600 g) | p-toluenesulfonic acid (18 g) | IPA (400 g) |

IPA is isopropyl alcohol

Also disclosed is the reaction of the epoxidized cardanol with compounds having at least one amine group under a similar processing conditions. The preferred is diethanol amine as disclosed in experiment 6.

The following procedure was used to prepare the plasticizers:

The materials described in Table II were introduced into a 5 liter round bottom flask with stirring, heating, a thermometer and water condenser. The contents were kept under atmospheric reflux was for 4 hours. The final epoxy number in all cases was zero at the end of all reactions. There was no separation of the composition; the entire composition was used as the plasticizer.

We claim:

1. A plasticizer composition comprising the reaction product of a first compound which is an alcohol selected from the group consisting of ethanol, isopropyl alcohol, and tert-butyl alcohol with a second compound which is an epoxidized molecule having at least 15 carbon atoms and 3 double bonds in the epoxidized molecule wherein the epoxidized molecule has a 15 carbon aliphatic chain in the meta position and is of the formula

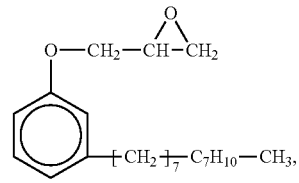

and the reaction product is void of expoxy groups.

2. The plasticizer composition of claim 1, wherein the epoxidized molecule is an epoxidized cardanol.

3. The plasticizer composition of claim 1, wherein the first compound is ethanol.

4. The plasticizer composition of claim 1, wherein the first compound is isopropyl alcohol.

5. The plasticizer composition of claim 1, wherein the plasticizer composition has been mixed with a thermoplastic compound.

6. The composition of claim 5, wherein the thermoplastic compound is polypropylene or a copolymer of polypropylene.

7. The composition according to claim 5, wherein the plasticizer is present from about 0.5 to about 12 weight percent of the total composition.

8. The composition according to claim 7, wherein the composition further comprises a flame retardant composition.

9. A plasticizer composition comprising a compound which is void of epoxy groups of the formula:

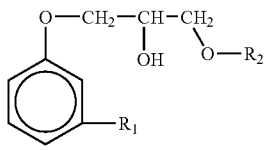

where $R_1$ is a 15 carbon atom aliphatic chain containing three non-conjugated double bonds and has the formula —[$CH_2$]$_7$—$C_7H_{10}$—$CH_3$ and $R_2$ is selected from the group consisting of the structures of ethanol, the structures of the isomers of propanol and the structures of the isomers of butanol without the OH group, and the oxygen attached to the $CH_2$, group and $R_2$ is bonded to any carbon of $R_2$.

10. A plasticizer of claim 9, having the formula of:

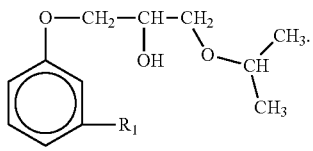

11. The plasticizer of claim 9, wherein the plasticizer has been mixed with a thermoplastic and a flame retardant composition and the flame retardant composition comprises a compound selected from the group consisting of a melamine, a diamine, magnesium hydroxide and aluminum hydroxide.

12. The plasticizer of claim 10, wherein the plasticizer has been mixed with a thermoplastic and a flame retardant composition and the flame retardant composition comprises at least one compound selected from the group consisting of a melamine, a diamine, magnesium hydroxide and aluminum hydroxide.

13. A process for the manufacture of a plasticizer compound comprising the steps of heating a mixture of an epoxidized oil and a first compound selected from the group consisting of ethanol, the isomers of propanol, the isomers of butanol and amines, in the presence of an acid catalyst and reacting the epoxidized oil with the first compound until at least less than 10% of epoxidized oil remains, and removing the excess alcohol.

14. The process of claim 13, wherein the epoxidized oil is epoxidized cardanol.

15. The process of claim 13, wherein the epoxidized oil comprises at least one compound having a 15 carbon aliphatic chain in the meta position with the compound having the formula

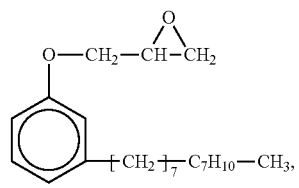

and the 15 carbon aliphatic chain in the meta position has three conjugated double bonds.

16. The process of claim 13, wherein the alcohol is selected from the group consisting of ethanol, the isomers of propanol and the isomers of butanol.

17. The process of claim 14, wherein the heating is done at reflux conditions.

18. The process of claim 15, wherein the heating is done at reflux conditions.

19. The process of claim 13, wherein the heating is done at reflux conditions.

20. The process of claim 16, wherein the heating is done at reflux conditions.

* * * * *